United States Patent [19]
Katz et al.

[11] Patent Number: 5,730,144
[45] Date of Patent: Mar. 24, 1998

[54] METHOD AND APPARATUS FOR PREDICTING THE EFFICACY OF CARDIOVERSION

[75] Inventors: Richard A. Katz, East Lyme, Conn.; Shalabh Chandra, Cleveland Heights, Ohio; Richard A. Grimm, Chagrin Falls, Ohio; James D. Thomas, Beachwood, Ohio

[73] Assignee: The United States of America as represented by the Secretary of the Navy, Washington, D.C.

[21] Appl. No.: 687,099

[22] Filed: Jul. 10, 1996

[51] Int. Cl.$^6$ .............. A61B 5/026; A61B 5/02; A61B 5/0285

[52] U.S. Cl. .............. 128/713; 128/695; 607/6

[58] Field of Search .............. 128/695, 713; 607/6

[56] References Cited

U.S. PATENT DOCUMENTS

| | | | |
|---|---|---|---|
| 4,841,981 | 6/1989 | Tanabe et al. | 128/713 |
| 5,183,040 | 2/1993 | Nappholz et al. | 128/661.07 |
| 5,243,976 | 9/1993 | Ferek-Petric et al. | 607/6 |
| 5,316,001 | 5/1994 | Ferek-Petric et al. | 128/662.06 |
| 5,438,983 | 8/1995 | Falcone | 128/713 |
| 5,507,780 | 4/1996 | Finch | 607/6 |

Primary Examiner—William E. Kamm
Assistant Examiner—Carl H. Layno
Attorney, Agent, or Firm—Michael J. McGowan; Prithvi C. Lall; Michael F. Oglo

[57] ABSTRACT

An apparatus and method for predicting the efficacy of cardioversion as a modality for reverting a patient with atrial fibrillation to normal sinus rhythm. Blood flow through the patient's atrium is measured, converted and processed using nonlinear or chaotic processing to obtain a differential radius signal. The number of excursions of the differential radius beyond a threshold value indicates whether cardioversion will be successful.

20 Claims, 5 Drawing Sheets

METHOD AND APPARATUS FOR PREDICTING THE EFFICACY OF CARDIOVERSION

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

(1) Field of the Invention

This invention generally relates to methods and apparatus for performing medical diagnoses and particularly to a method and apparatus for predicting the efficacy of cardioversion for reverting a fibrillating heart to normal sinus rhythm.

(2) Description of the Prior Art

Atrial fibrillation represents a significant disease of the heart. Generally a heart disease diagnosis involves an analysis of EKG data, generally by identifying visually certain patterns or anomalies in an EKG recording. Visual inspection of an EKG recording remains a primary diagnostic tool even though a number of complementary or superseding computer assisted modalities have been suggested.

For example, U.S. Pat. No. 5,191,524 to Pincus et al. discloses a method and apparatus for diagnosing medical conditions by analyzing data, such as EKG data, to determine the approximate entropy in the signal by comparing subsets of data to reveal the regularity and stability of similar patterns amongst the data subsets. The contribution of noise to measurement of the regularity and stability is minimized. Quantitative values are assigned to measure the degree of regularity and stability. From these quantitative values a single output measure is generated indicative of the amount of the patterness of the sequence of data. The calculations required to determine the approximate entropy are preferably performed within a data processing system.

Another system, as disclosed in U.S. Pat. No. 5,105,354 to Nishimura, discloses a method for forecasting sudden infant death syndrome by investigating the correlation between respiration and heart beat in both a normal state and a sleep apnea state of a newborn. In essence the system detects respiratory information, produces an envelope indicative of the respiration information and samples the envelope to produce a fast Fourier transform spectrum of the envelope information. Simultaneously the system detects cardio-electric information in the form of an EKG, detects the peak value and calculates a sequential R—R interval series that is fast Fourier transformed into a spectrum of the R—R interval variation. These two complex conjugations are multiplied and, through a fast Fourier transform, analyzed to calculate a correlation between respiration and heart beat that can then be evaluated to identify the state just before the normal state of a newborn will convert to the state of sleep apnea and forecast sudden death syndrome.

It has also been recognized that cardio and respiratory signals are signals of non-linear dynamical systems. U.S. Pat. No. 5,404,298 to Wang et al. and 5,453,940 to Broomhead et al. disclose dynamical system analyzers or chaos analyzers useful in determining characteristics based upon such dynamical system signals. Additional information on the use of chaos is contained in Strogatz, Steven H., *Nonlinear Dynamics in Chaos*, Reading, Mass., Addison Wellsley Publishing Company, 1994, p. 379.

As presently understood, none of the systems described in the foregoing references or elsewhere suggests a method or system that would readily predict the efficacy of any process for enabling a patient's heart to revert from atrial fibrillation to a normal sinus rhythm. The normal process of choice for personnel making such a diagnosis remains the classical analysis of raw data information, as from an EKG over time, in light of experience or a priori knowledge in the field. It is on this basis that a physician tries to predict whether cardioversion or other modality is appropriate to reverting a heart to normal sinus rhythm.

SUMMARY OF THE INVENTION

Therefore it is an object of this invention to provide a method and apparatus for analyzing characteristics of a fibrillating heart.

Another object of this invention is to provide a method and apparatus for predicting the efficacy of cardioversion in reverting a heart from atrial fibrillation to a normal sinus rhythm.

The method and apparatus of this invention are based upon an in situ measurement of blood flow through a patient's atrium and manipulation of a corresponding velocity signal representing the velocity of blood flow over a diagnostic time interval. Chaotic and differential processing converts the velocity signal into a differential radius signal. The number of instances that the differential radius signal exceeds a threshold value indicates whether the patient is susceptible to a return to sinus rhythm by cardioversion.

BRIEF DESCRIPTION OF THE DRAWINGS

It is the intent of the appended claims to point out with particularity and to claim distinctly the subject matter of this invention. The various objects, advantages and novel features of this invention will be more fully apparent from a reading of the following detailed description in conjunction with the accompanying drawings in which like reference numerals refer to like parts, and in which:

DESCRIPTION OF THE PREFERRED EMBODIMENT

Figure 1:
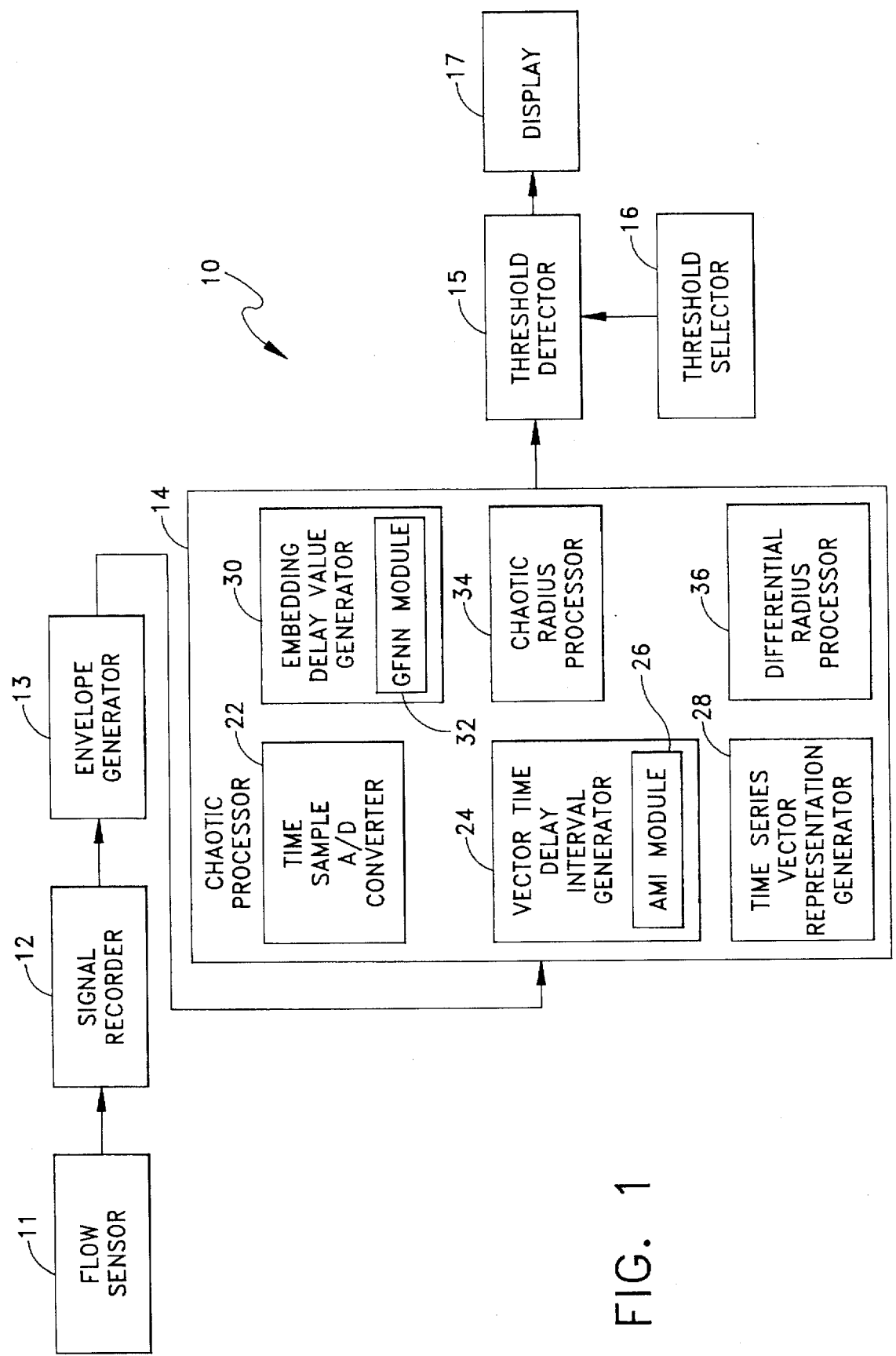
FIG. 1 is a block diagram of apparatus for implementing this invention.

Apparatus 10 embodying this invention includes a flow sensor 11 for developing a signal based upon transesophegeal Doppler echocardiography modality. In this modality a physician inserts a Doppler flow sensor through an endoscope into the esophagus of the patient and orients the ultrasonic transducer immediately behind the left atrium with an imaging plane adjusted to visualize the left atrial appendage. Known pulse Doppler echocardiographic techniques direct short bursts of sound energy toward the left atrium. Return echoes within an appropriate time window determined by the range of the target from the transducer produce an output signal.

A signal recorder 12 converts the output signal from the flow sensor 11 over a diagnostic interval into a record of the velocity signal. For this particular application, the diagnostic time interval can be in the order of three to five seconds. In one embodiment the signal recorder 12 comprises a conventional strip chart recorder that produces a strip chart that represents the velocity along a Y-axis and time along an X-axis. Alternatively the signal recorder 12 could generate an electrical signal representing the flow over time.

In such a system it is known that at any instant of time there is more than one velocity recorded from the sample volume. An envelope generator 13 records the maximum measurement velocity at each instant. The envelope generator 13 could comprise a signal processor for converting a continuous signal from the signal recorder 12 to an envelope signal or could comprise apparatus for enabling the production of a manual trace of the maximum values from a strip chart recorder.

A chaotic processor 14 converts the signal from the envelope signal from the generator 13 into a differential radius signal that exhibits a marked propensity for an increasing number of deflections and an increased magnitude of deflections as the possibility decreases that cardioversion will be successful. The operation of the processor 14 will be described in more detail later. A threshold detector 15 counts each excursion of the differential radius beyond a threshold level set by a threshold selector 16. A display 17 can display the resulting differential radius and threshold information to enable an operator to count the excursions or can provide the count automatically. If this count is below a minimum level the patient is a good candidate for successful cardioversion. Conversely, if the number of excursions is greater than that value, there is little likelihood that cardioversion will be successful.

Figure 2:
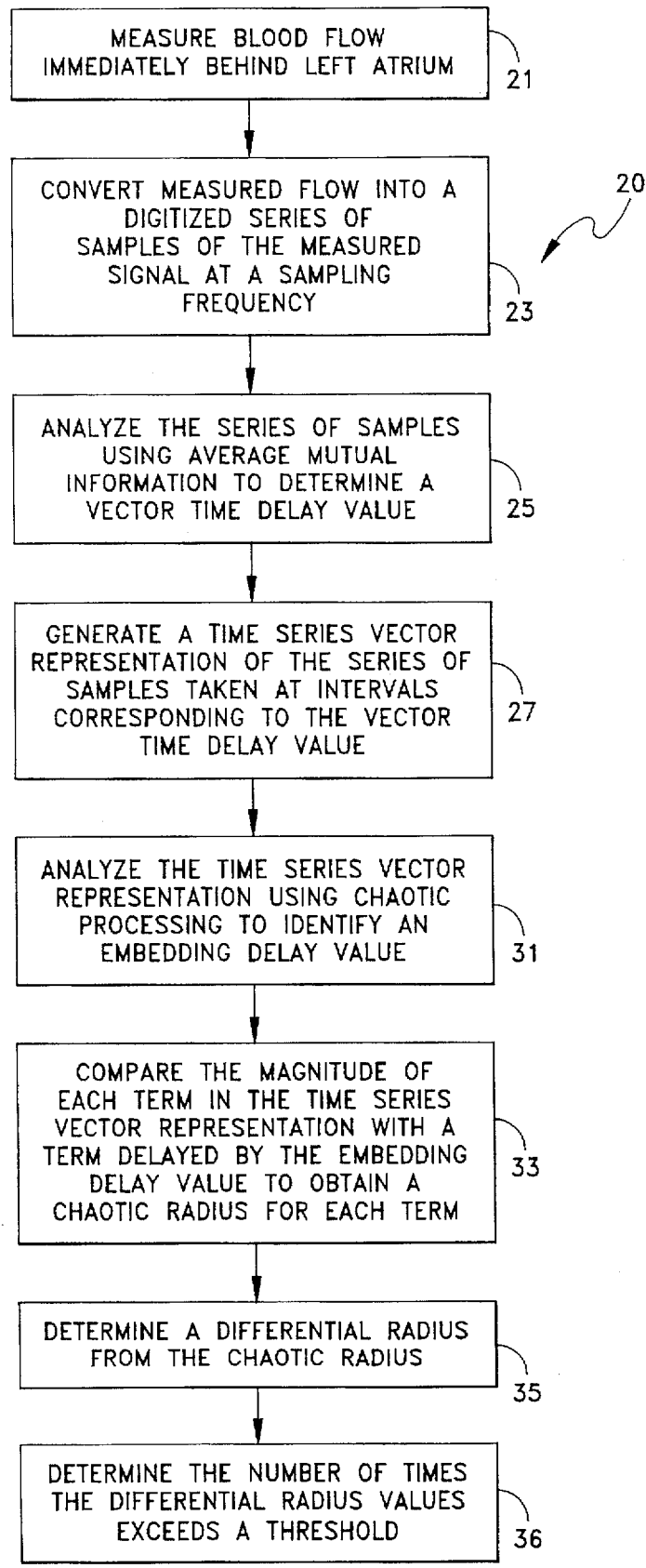
FIG. 2 is a flow chart representing the method employed by the apparatus in FIG. 1 in accordance with this invention.
Figure 3A:
FIGS. 3A and 3B depict an EKG signal for two patients.
Figure 4A:
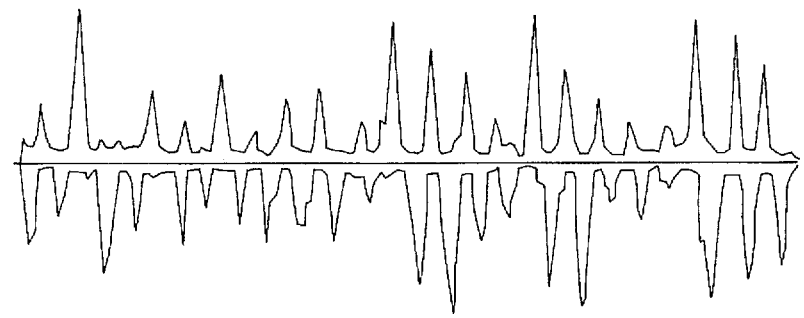
FIGS. 4A and 4B represent the blood flow signal obtained for the two patients of FIGS. 3A and 3B.
Figure 5A:
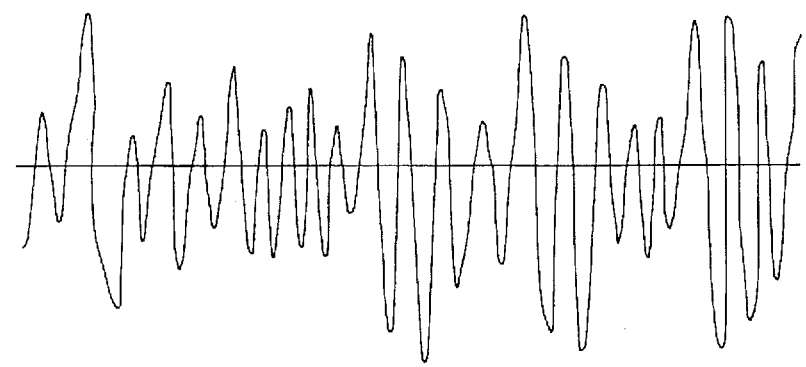
FIGS. 5A and 5B represent signals derived from the signals shown in FIGS. 4A and 4B respectively.
Figure 3B:
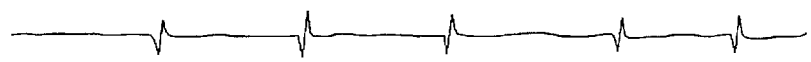
Figure 4B:
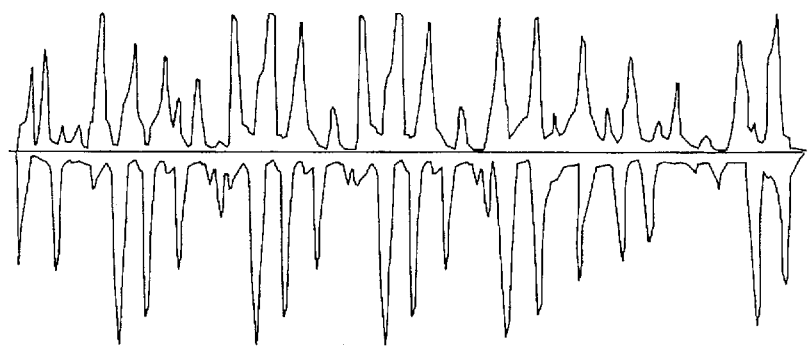
Figure 5B:
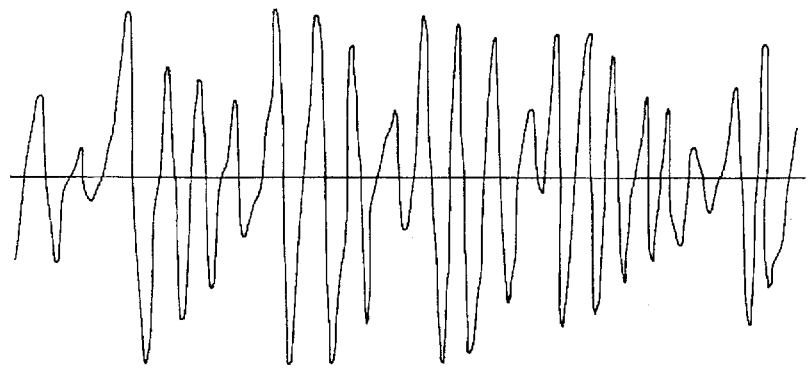

FIG. 2 depicts the steps in one method 20 for predicting the efficacy of cardioversion that includes, as an initial step 21, the measurement of the blood flow immediately behind the left atrium. This function can be produced by the flow sensor 11 and signal recorder 12 in FIG. 1. Generally the diagnosis will also record other cardiac information, such as depicted in FIGS. 3A and 3B that constitute EKG recordings for two patients diagnosed with atrial fibrillation. FIGS. 4A and 4B depict the signal from a chart recorder acting as the signal recorder 12. FIGS. 5A and 5B depict the signal that the envelope generator 13 produces for each of signal sets of FIGS. 4A and 4B respectively. The signals in FIGS. 5A and 5B are converted into a series of discrete digital scalar values at a sampling frequency. The sampling frequency must be selected to provide adequate sampling so that following steps in the process will have sufficient data for providing reliable results with a reasonable temporal resolution. Over-sampling is preferable to under-sampling even though this increases the burdens of processing time and complexity. It has been found that the minimum sampling frequency ought to be from six to ten times the Nyquist sampling frequency for signals in FIGS. 5A and 5B. Given the time scales of cardiac cycles, a sampling frequency of 2 kHz has been found to be a good compromise between the sampling objectives and burdens that significant over-sampling would impose on the system.

Referring to FIGS. 1 and 2, a time sample A/D converter 22 in the processor 14 converts the analog envelope signal into a sampled digital representation of the signal shown in FIGS. 5A and 5B that represent, at each instant, the maximum magnitude of the flow value in the sample volume. More specifically, the converter 22 and step 23 in FIG. 2 produce a digitized representation of each of the graphs shown in FIGS. 5A and 5B into corresponding scalar time series having the general form:

$$v(n)=v(t+ndt) \tag{1}$$

where "t" is the start time for the diagnosis, "dt" is the sample interval (e.g., 0.0005 seconds at a 2 kHz sampling frequency) and "n" is the sample number and n=1, 2, 3, ... . N.

A vector time delay interval generator 24 in FIG. 1 processes this scalar time series to determine an interval at which a series of vectors should be generated. This process can use several known techniques. One is a linear auto-correlation technique. When the results of the auto-correlation technique are plotted, the interval to the first zero crossing can be selected as the vector time delay.

Step 25 in FIG. 2 depicts a preferred alternative that uses a known average mutual information (AMI) process, represented by an AMI module 26 in FIG. 1, to determine the vector time delay. As known, average mutual information quantitates the information theoretic properties of chaotic systems. More specifically, average mutual information indicates how much information exists in the form of a time series such as shown in Equation 1 concerning the measurement of that signal at a time Tdt later. That is, a time series v(n) for average mutual information indicates how much information will be available to predict the voltage level at a time Tdt later, i.e., the value v(n+T). Average mutual information processes distribute the measurements v(n) and v(n+T) over the set of measured data and determine the joint distribution of measurements of these two quantities. The first of these distributions is P(v(n)), the second is P(v(n+T), and the third is P(v(n),v(n+T)). The mutual information between these measurements is:

$$\ln\left[\frac{P(v(n),v(n+T))}{P(v(n))P(v(n+T))}\right] \tag{2}$$

where "ln" is the natural logarithm. For N observations, the average over all measurements is the AMI given by:

$$AMI = \sum_{n=1}^{N}\left[P(v(n),v(n+T))\ln\frac{P(v(n),v(n+T))}{P(v(n))P(v(n+T))}\right] \tag{3}$$

For independent measurements, each term in the above sum vanishes due to factorization of the joint probability P(a,b)=P(a)P(b). For the case T=0, I(0) is large because there is full knowledge of the measurements. Generally, however, I(T) will be greater than zero. The objective becomes determining an intermediate value that will preserve the information in the system without overburdening the process. With average mutual information, one approach is to choose the value for T that corresponds to the first minimum of I(T), although any value of T near the first minimum should suffice. As will be apparent the value of T can be any arbitrary number. Normally, the value will be refined so that it corresponds to an integer multiple of the sampling integral established in the converter 22.

Once the value T has been obtained, step 27 in FIG. 2 uses a time series vector representation generator 28 in the chaotic processor 13 to convert the digitized samples into a time series vector representation that has a sampling interval of T. Each vector points to the scalar value at an interval "T" later. More specifically the time series vector generator 28 in FIG. 1 operating in accordance with step 27 in FIG. 2 generates a d-dimensional set of vectors from a sequence of fixed vector time delays, T, in the form:

$$y(n) = v(n), v(n+T), v(n+2T), \ldots v(n+(d-1))T \quad (4)$$

where:

v(n) is the original time series datum at time index n;

v(n+T) is datum from the same time series offset in the positive direction by the vector time delay interval T;

v(n+2T) is datum from the same time series offset in the positive direction by the vector time delay interval 2T;

v(n+d−1)T is the datum offset by the vector delay interval (d−1)T where d is an embedding dimension to be obtained from an embedding delay value generator 30 in FIG. 1 as it processes step 31 in FIG. 2; and n is an index number for time series datum where n=1, 2, 3 ... N and the maximum number of indices, N, may be selected to be any value.

The resulting time series vector is then analyzed to determine a minimum embedding function, "d". As with respect to the generation of the vector time delay interval, alternate approaches are available for determining the embedding delay value. A preferred approach that has produced reliable results utilizes a known "global false nearest neighbor" process that is implemented in the generator 30 by an GFNN module 32. Basically this process is based upon the concept that when points of higher dimension are projected down to a space of lower dimension, there are overlapping orbits in the low dimension space such that if the process were reversed and given space were projected to a higher dimension it could be reasonably expected that neighboring points along a trajectory would separate. Basically the process starts with a first dimension, unfolds the time series vector representation to higher and higher dimensions while keeping track of the percentage of nearest neighbors that spread apart at each integer increase of dimension. When the quality of the other producing the desired result constitutes the minimum embedding value.

More specifically the process determines the dimension "d" with points made out of the vector representation in which the nearest neighbors ynn(n) of the point y(n) is given by:

$$ynn(n) = [vnn(n), vnn(n+T) \ldots vnn(n+(d-1)T)] \quad (5)$$

The process determines whether or not these points remain near in dimension (d+1), when vector y(n) is augmented by a component v(n+dT) and ynn(n) is augmented by vnn(n+dT). For small distances the neighbors are true neighbors. For large distances false neighbors exist. When the percentage of false neighbors drops to zero, the resulting delay is the minimum embedding dimension or delay value.

Figure 6:
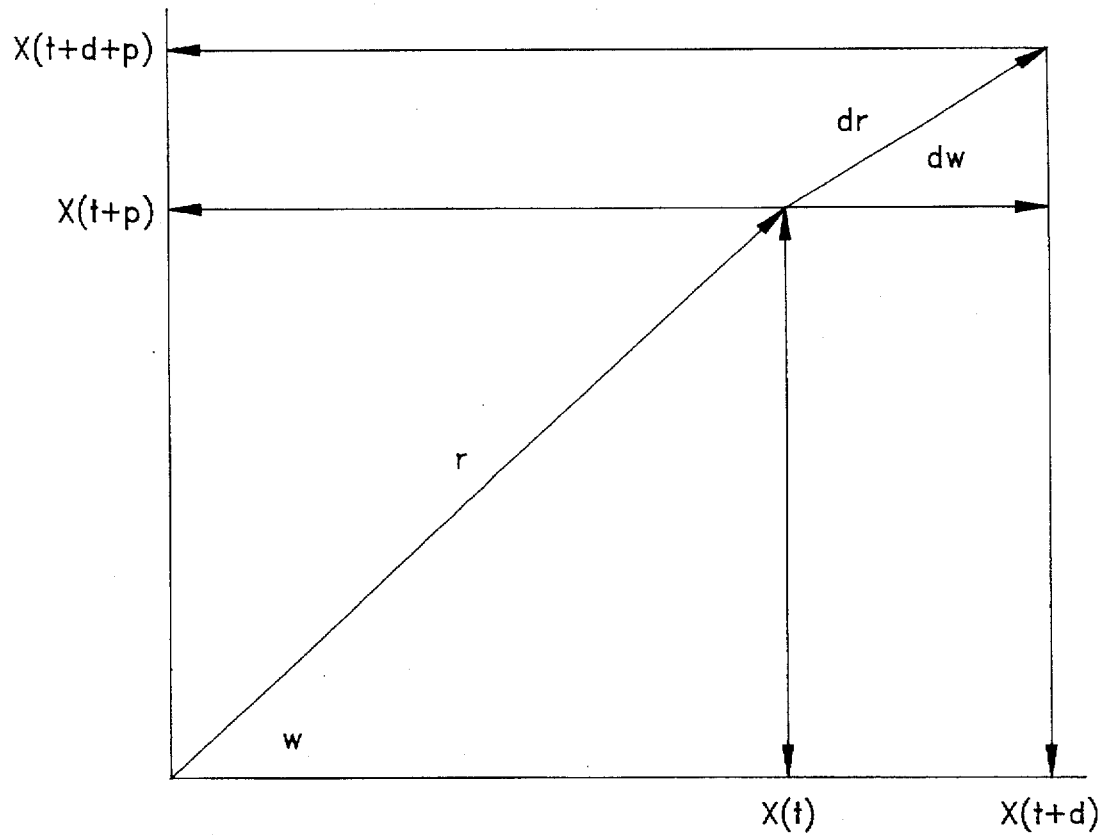
FIG. 6 is a diagram useful in understanding the operation of the apparatus and method of FIGS. 1 and 2.

Once the minimum embedding delay value has been determined, step 33 in FIG. 2 and a chaotic radius processor 34 in FIG. 1 compare the magnitude of each term in the time series vector representation with a term delayed by the embedding delay value to obtain a chaotic radius for each term. More specifically, the chaotic radius processor 34 in FIG. 1 effectively plots the scalar value of each point in the vector series as shown in FIG. 6. On a horizontal scale and a vertical scale, X(t) and X(t+p) represent the component magnitudes of the vector at time "t"; points X(t+d) and X(t+d+p) respectively represent the change in magnitude between two successive points at "t" and at (t+d). Consequently the chaotic radius (r) is given by:

$$r = \sqrt{X(t)^2 + X(t+p)^2} \quad (6)$$

It will be further evident that the differential radius (dr) can be determined by:

$$dr = \sqrt{[X(t+d) - X(t)]^2 + [X(t+d+p) - X(t+p)]^2} \quad (7)$$

or by $$dr = r(i+1) - r(i) \quad (8)$$

Figure 7A:
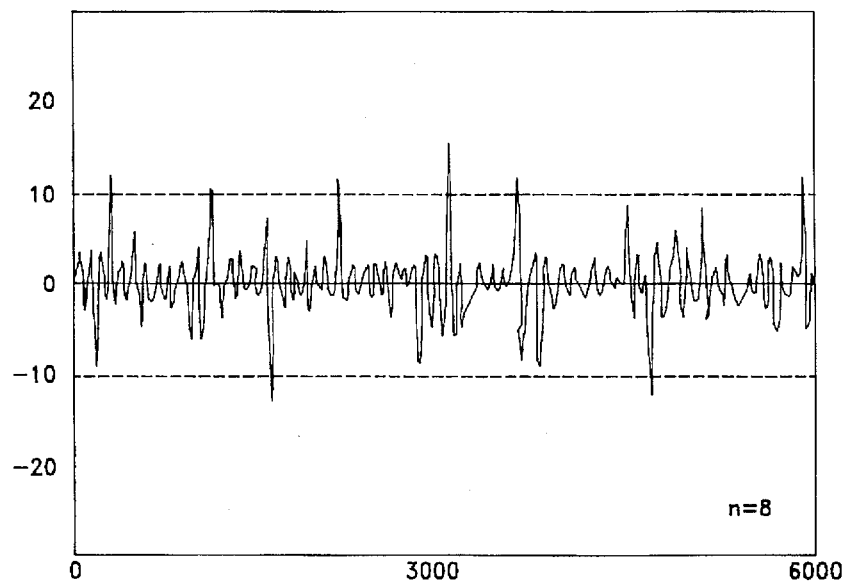
FIGS. 7A and 7B depict an output signal for the measurements obtained in FIGS. 3A and 3B and FIGS. 4A and 4B in accordance with this invention.
Figure 7B:
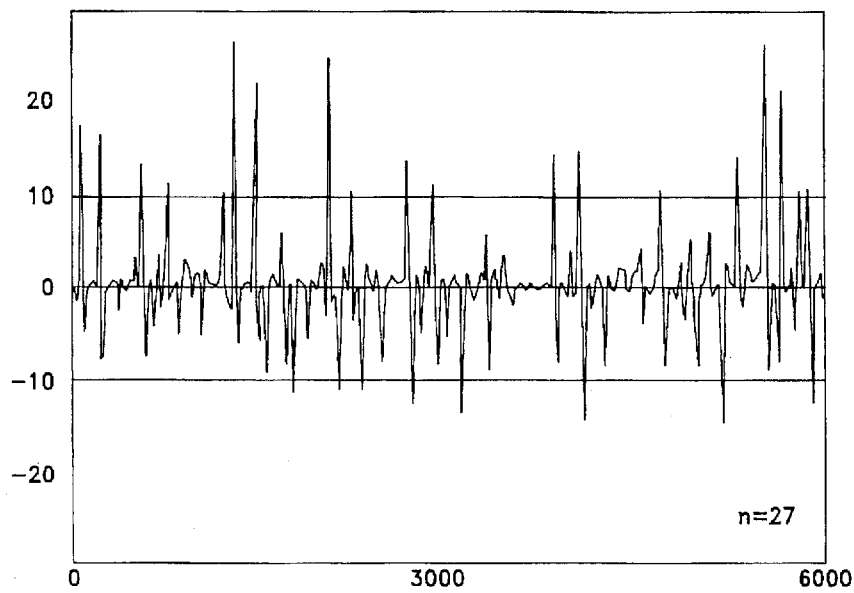

Step 35 in FIG. 2 and a differential radius processor 36 in FIG. 1 compute, for each vector in the time series vector representation, a corresponding differential radius, dr, according to either of the foregoing alternatives. FIGS. 7A and 7B display the differential chaotic radius for the measurements obtained in FIGS. 4A and 4B, respectively, using the second alternative.

FIGS. 7A and 7B also depict a threshold value set at 10 such that the differential radius exceeds the threshold eight times for the patient represented by the measurements in FIGS. 4A and twenty-seven times for the patient represented in FIG. 4B. The threshold selector 16, as previously indicated, establishes this threshold. Typically the selection of a particular threshold value can be determined empirically. As will be apparent, if the threshold is set too low, the number of excursions will be very high. Conversely, if the threshold is if set very high (e.g., greater than 30) there would be no excursions. A graph representing the relationship between the number of excursions beyond a threshold as a function of threshold value, typically will produce a plateau at some intermediate threshold level. The selection of a value at the center of that plateau will produce good results. Moreover, it will also be apparent that a threshold value of "10" indicates an excursion will be counted if it is greater than +10 or less than −10.

Whatever the form, the number of excursions then become a quantification metric for the diagnosis, and this quantification metric becomes the predictor for cardioversion outcome. Low values indicate predicted cardioversion success and high values predict failure. For the patients represented by the measurements in FIGS. 4A and 4B, FIGS. 7A and 7B predict a cardioversion success for the first patient (N'=8) and cardioversion failure for the second patient (N'=27). To date the readings of different patients have fallen into statistically different groups. Consequently, a go-no go decision might be made based upon different values of "n". For example, success might be predicted on N'<10 while failure might be predicted on N'>20. Nevertheless, the outer ranges represent a significant patient population. Moreover, it is expected that as data is accumulated over time, the magnitude of the intermediate range will decrease so that the percentage of successful predictions will increase.

It now will be apparent that in accordance with this invention nonlinear signal processing applied to flow velocity measurements of patients with atrial fibrillation can be an efficacious predictor of the success of cardioversion. Moreover, the apparatus and method of this invention provide other information about atrial fibrillation that can be analyzed for understanding the mechanisms thrombogenesis and thromboembolism in predicting patients who are likely to have these complications. Transesophegeal Doppler echocardiography represents one approach for obtaining the flow data. It will be apparent, however, that a number of variations are possible for determining the flow. The envelope generator 12 shown in FIG. 1 can incorporate the manual steps of converting signals from a strip chart recorder or can include electronic and data processing circuits for monitoring the signal and producing the envelope of the maximum values as a function of time. Any number of available chaotic processing systems can be utilized to generate the information provided by the chaotic processor 14 shown in FIG. 1. The individual components in FIG. 1, particularly those in the processor 14 and threshold detector 15 may comprise discrete structures or software modules in a data processing system or a hybrid. The display 17 of the system 10 in FIG. 1 can comprise a simple graphical display of the differential radius against a threshold or a circuit for comparing the values of the differential chaotic radius against the thresholds and automatically computing an index which would indicate that the likelihood of cardioversion success.

Therefore, it is the intent of the appended claims to cover all such variations and modifications as come within the true spirit and scope of this invention.

What is claimed is:

1. A method for determining the likelihood that cardioversion will cause a patient with atrial fibrillation to revert to normal sinus rhythm cardioversion including the steps of:
 monitoring the flow of blood through the patient's atrium;
 generating a velocity signal representing the velocity of blood flow over a diagnostic time interval including a plurality of cardiac cycles;
 generating a differential radius signal based upon chaotic and differential processing of the velocity signal over the diagnostic time interval; and
 determining the number of instances that the differential radius signal exceeds a threshold value over the diagnostic time interval thereby to indicate whether the patient will revert to normal sinus rhythm by cardioversion.

2. A method as recited in claim 1 wherein said generation of said differential radius signal includes the step of digitizing the velocity signal to obtain a series of time samples at a sampling frequency.

3. A method as recited in claim 2 wherein said generation of the differential radius signal includes generating a time series vector representation for the series of time samples.

4. A method as recited in claim 3 wherein said generation of the differential radius signal includes:
 generating an embedding delay value based upon the time series vector representation;
 comparing the magnitudes of the terms of the vector representation at a given time and at a time delayed by the embedding delay value to obtain a chaotic radius; and
 generating in response to each value of the chaotic radius the differential chaotic radius for the given time.

5. A method as recited in claim 4 wherein said step of determining an embedding delay includes:
 generating a vector time delay interval in response to the data in the time series of samples; and
 generating the time series vector representation based upon the value of the data in the time samples at intervals corresponding to the vector time delay interval.

6. A method as recited in claim 5 wherein said step of generating the vector time delay interval includes the step of obtaining average mutual information from the time series of samples.

7. A method as recited in claim 5 wherein said generation of the embedding delay value includes the step of obtaining global false nearest neighbor information from the time series vector representation.

8. A method as recited in claim 5 wherein said step of generating the differential chaotic radius includes comparing, at times corresponding to each vector time delay interval, the magnitude of the time series vector representation at that time and the magnitude of the time series vector representation at time offset by the embedding delay value.

9. A method as recited in claim 8 wherein said step of determining the threshold value includes selecting a value from a range of threshold values that define statistically significant data.

10. A method as recited in claim 5 wherein said step of generating the differential chaotic radius includes comparing, at times corresponding to each vector time delay interval, the magnitude of the time series vector representation at that time and the magnitude of the time series vector representation at time offset by the embedding delay value and wherein:
 the sampling frequency is in the range of six to ten times the Nyquist sampling frequency for the velocity signal;
 the vector time delay is an integer multiple of the sampling interval; and
 the embedding function is an integer multiple of the vector time delay.

11. Apparatus for determining the likelihood cardioversion will cause a patient with atrial fibrillation to revert to normal sinus rhythm, said apparatus comprising:
 means for monitoring the flow of blood through the patient's atrium;
 first generating means for generating a velocity signal representing the velocity of blood flow over a diagnostic time interval including a plurality of cardiac cycles;
 second generating means for generating a differential radius signal based upon chaotic and differential processing of the velocity signal over the diagnostic time interval; and
 threshold evaluation means for determining the number of instances that the differential radius signal exceeds a threshold value over the diagnostic time interval thereby to indicate whether the patient will revert to normal sinus rhythm by cardioversion.

12. Apparatus as recited in claim 11 wherein said second generating means includes means for digitizing the velocity signal to obtain a series of time samples at a sampling frequency.

13. Apparatus as recited in claim 12 wherein said second generating means includes means for generating a time series vector representation for the series of time samples.

14. Apparatus as recited in claim 13 wherein said second generating means includes:
 means for generating an embedding delay value based upon the time series vector representation;
 means for comparing the magnitudes of the terms of the vector representation at a given time and at a time delayed by the embedding delay value to obtain a chaotic radius; and
 means for generating in response to each value of the chaotic radius the differential chaotic radius for the given time.

15. Apparatus as recited in claim 14 wherein said second generator means includes:
 means for generating a vector time delay interval in response to the data in the time series of samples; and
 time series vector representation generating means responding to the values of the data in the time samples at intervals corresponding to the vector time delay interval.

16. Apparatus as recited in claim 15 wherein said means for generating the vector time delay interval includes means for obtaining average mutual information from the time series of samples.

17. Apparatus as recited in claim 15 wherein said means for generating the embedding delay value includes means for obtaining global false nearest neighbor information from the time series vector representation.

18. Apparatus as recited in claim 15 wherein said second generating means includes means for comparing, at times corresponding to each vector time delay interval, the magnitude of the time series vector representation at that time and the magnitude of the time series vector representation at time offset by the embedding delay value.

19. Apparatus as recited in claim 18 wherein means for said threshold evaluation means includes means for selecting a value from a range of threshold values that define statistically significant data.

20. Apparatus as recited in claim 15 wherein said second generating means includes means for comparing, at times corresponding to each vector time delay interval, the magnitude of the time series vector representation at that time and the magnitude of the time series vector representation at time offset by the embedding delay value and wherein:

said digitizing means operates at a sampling frequency in the range of six to ten times the Nyquist sampling frequency for the velocity signal;

the vector time delay is an integer multiple of the sampling interval; and the embedding function is an integer multiple of the vector time delay.

* * * * *